United States Patent [19]

Fitz

[11] Patent Number: 5,092,328
[45] Date of Patent: Mar. 3, 1992

[54] MOUTHPIECE ASSEMBLY WITH DISPOSABLE LINER FOR BREATHING APPARATUS

[76] Inventor: Edward Fitz, 27 Llaanfair Rd., Ardmore, Pa. 19003

[21] Appl. No.: 631,880

[22] Filed: Dec. 21, 1990

Related U.S. Application Data

[62] Division of Ser. No. 401,848, Aug. 31, 1989, Pat. No. 4,991,575.

[51] Int. Cl.⁵ .................... A61M 16/00; A62B 9/06
[52] U.S. Cl. .................... 128/207.14; 128/200.26; 128/911
[58] Field of Search ........... 128/200.24, 200.26, 128/207.14, 207.29, 204.18, 205.27, 204.26, 206.17, 206.19, 205.25, 206.21, 206.23, 206.24, 911

[56] References Cited

U.S. PATENT DOCUMENTS

| | | |
|---|---|---|
| 3,556,097 | 1/1971 | Wallace . |
| 3,802,428 | 4/1974 | Sherman . |
| 4,030,493 | 6/1977 | Walter et al. ............ 128/206.21 |
| 4,231,364 | 11/1980 | Speshyock ............ 128/207.14 |
| 4,719,911 | 1/1988 | Carrico ............ 128/206.19 |

Primary Examiner—Edgar S. Burr
Assistant Examiner—Lisa E. Malvaso
Attorney, Agent, or Firm—Stuart E. Beck

[57] ABSTRACT

A mouthpiece assembly for a breathing apparatus comprising a housing, a disposable liner, and a protective sheath. The housing comprises a conical opening extending therethrough. The liner is conical and is adapted to be received in the housing. A seal is provided between the liner and the housing to prevent leakage of air. The liner includes a member for engaging the lips of the user when the mouthpiece is in use. The sheath is located between the housing and the liner. Additionally, the liner includes alignment members which are suitable for aligning the liner with the housing and for spacing adjacent liners when they are stacked.

8 Claims, 2 Drawing Sheets

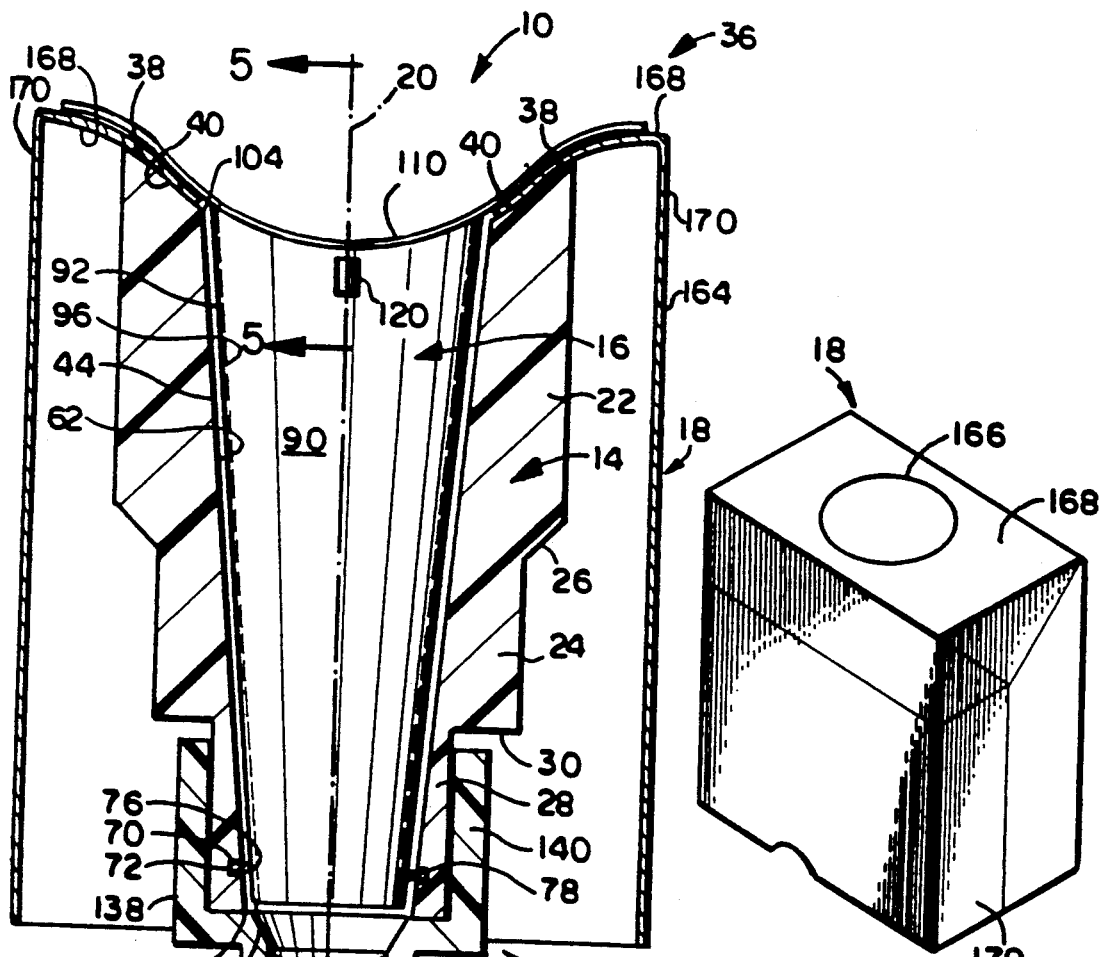
FIG. 1
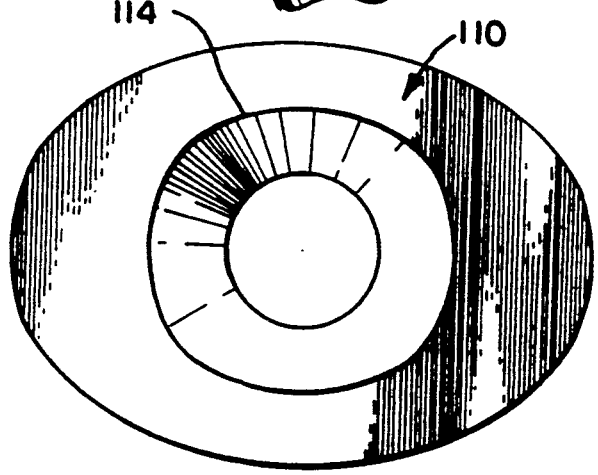
FIG. 3
FIG. 4

MOUTHPIECE ASSEMBLY WITH DISPOSABLE LINER FOR BREATHING APPARATUS

This application is a division, of application Ser. No. 07/401,848, filed Aug. 31, 1989, now U.S. Pat. No. 4,991,575 issued Feb. 12, 1991.

FIELD OF THE INVENTION

This invention relates to a mouthpiece assembly for a breathing apparatus and more particularly to a disposable liner therefor.

A common form of therapy for increasing the strength and capacity of the lungs is the inhalation and exhalation of gases such as air and the like.

Over the years, many devices for increasing the strength and capacity of the lungs have been developed.

Because the therapy requires the patient to inhale or exhale, these devices include a mouthpiece assembly. Typically, the mouthpiece assembly includes a portion which the patient takes into his mouth and holds between his lips in a manner similar to the way a straw is held.

The devices with which these mouthpieces are used are generally for providing therapy at low exhalation pressures. This is because if the patient exhales at high pressure, the force of the air leaving his lungs tends to force his lips away from the mouthpiece and permits air to leak from the device. This diminishes the effectiveness of the therapy.

Accordingly, it is desirable to have a mouthpiece assembly for a breathing apparatus which will enable the patient to exhale at high pressure while maintaining an airtight system so that the effectiveness of the therapy is maintained at its highest level.

Since a portion of the mouthpiece assembly for these devices must necessarily come into intimate contact with the mouth of the patient, it is important that it be sanitary.

A sanitary mouthpiece can be achieved by using a disposable liner, preferably made of low cost material.

Thus, the invention relates to a disposable liner for a mouthpiece for a breathing apparatus which comprises first and second members. The first member is frustoconical in shape and is comprised of a generally rigid material. The second member which is for contacting the pursed lips of a patient is comprised of a relatively thin element. It includes a central opening which is in engagement with the opening at the larger end of the first member.

In another aspect the invention relates to a mouthpiece assembly for a breathing apparatus which comprises a housing and a disposable liner. The housing includes an inner wall which defines an opening and the liner includes a portion that is slideably received by and disposed in the opening in the housing. Means on the housing define a bearing surface. The liner includes a member which lies against the bearing surface for contacting the pursed lips of a patient using the breathing apparatus. Seal means are provided between the housing and the liner.

BRIEF DESCRIPTION OF THE DRAWING

The invention will be better understood and further advantageous uses thereof will be readily apparent when considered in view of the following detailed description of a presently preferred embodiment, taken with the accompanied drawing in which:

FIG. 1 is a side elevation view partially in section of a mouthpiece assembly constructed in accordance with the presently preferred embodiment of the invention.

FIG. 3 is a plan view of the liner comprising the present invention.

FIG. 4 is a three-quarter view of a protective sheath for the invention.

DESCRIPTION OF THE PREFERRED EMBODIMENT

Figure 2:
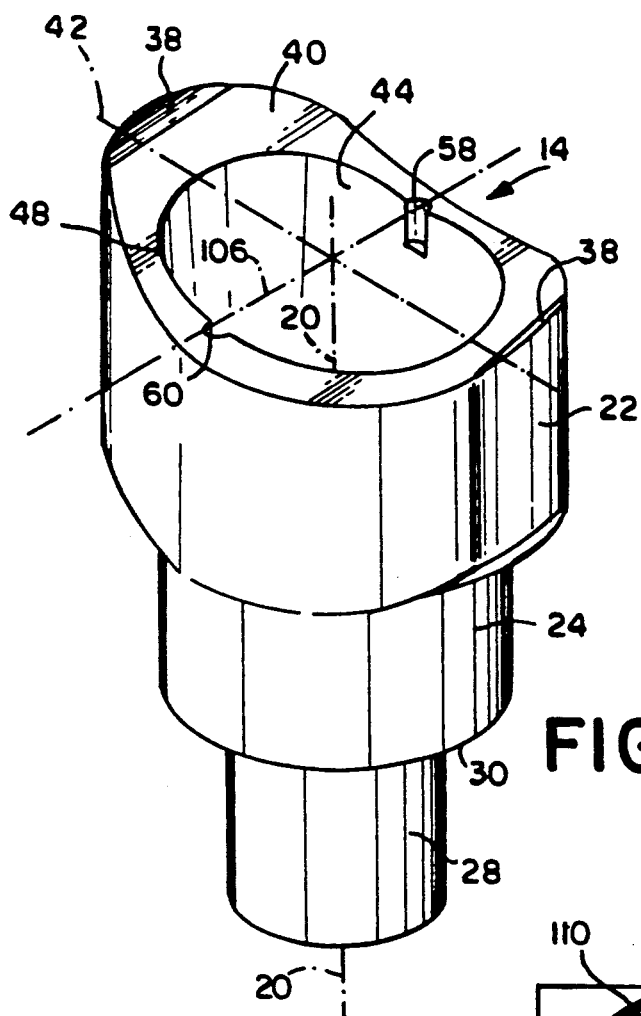
FIG. 2 is a three-quarter view of the housing comprising the present invention.

Referring to FIG. 1 the mouthpiece assembly 10 comprises a housing 14, a disposable liner 16 and a protective sheath 18. The housing 14 includes a longitudinally extending axis 20.

As best seen in FIGS. 1 and 2 the housing 14 may be made from a thermoplastic or other suitable non-toxic material such as nylon. It is comprised of several portions of different cross section.

In the preferred embodiment, housing 14 is comprised of several portions of different sizes. The largest portion 22 is adjacent the top of the housing and has an oval cross section. The next portion 24 is immediately adjacent the largest portion 22 and is disposed below it. Portion 24 may be cylindrical in cross section. The juncture of portions 22 and 24 is defined by ledge 26.

Immediately below cylindrical portion 24 is a second cylindrical portion 28. The juncture of portions 24 and 28 is defined by ledge 30.

The upper end 36 of the oval portion of housing 14 is recessed to accomodate the patient's mouth. The recess is defined by first and second curved surfaces 38 and 40 having axes (not shown) which are disposed at right angles (into the paper) to axis 20. First curved surface 38 is relatively flat compared to second curved surface 40 and lies outwardly thereof so that its two outer portions are present on each side of second curved surface 40. The major axis 42 (FIG. 2) of curved surfaces 38 and 40 lies parallel to the major axis of the oval cross section of portion 22.

The housing 14 includes a frusto-conical opening 44 that is coaxial with housing axis 20. The opening 44 has its larger end opening onto second curved surface 40 at 48 and its smaller end being defined by an opening 54 at the bottom of cylindrical housing portion 28.

Figure 5:
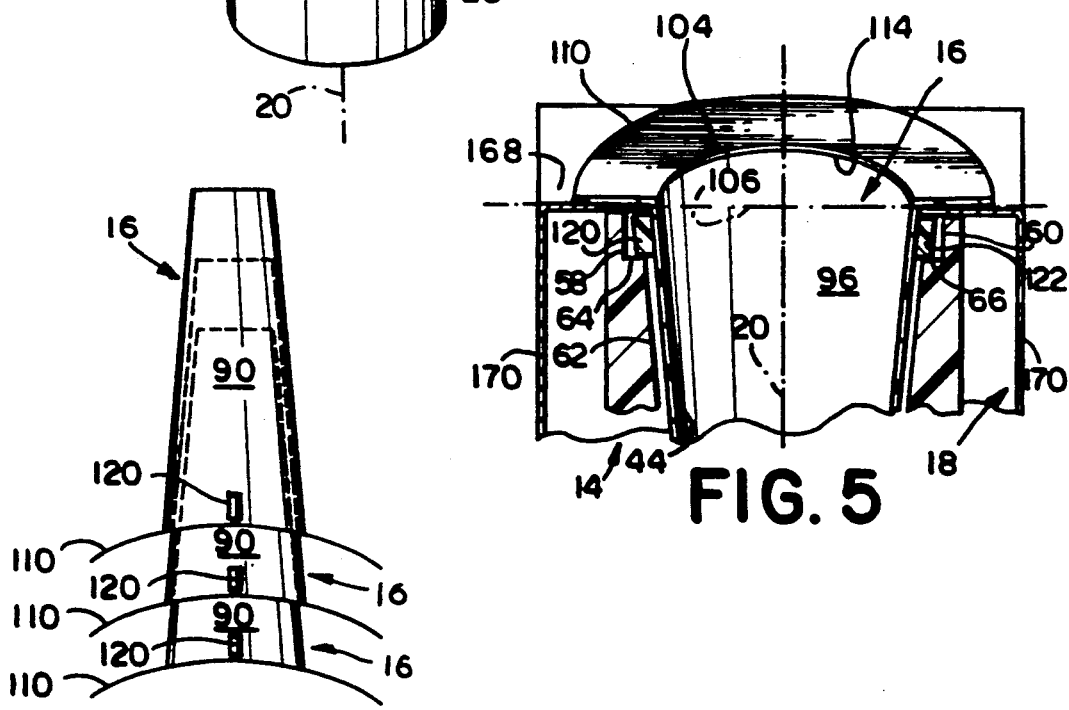
FIG. 5 is a view partially in section taken along line 5—5 of FIG. 1.

At the juncture of the opening 44 and surface 40 are two diametrically opposed recesses 58 and 60 (FIG. 5).

The recesses 58 and 60 are formed on the inner wall 62 of the conical opening 44 along its minor axis 106.

They extend downwardly into the inner side wall of the opening 44 a short distance where their ends are defined by ledges 64 and 66.

A sealing element 70 is provided at the lower end of conical opening 44. The sealing element may be made of resilient flexible material. It is an annulus with its outer wall 72 connected to the inner wall 62 of the opening 44. The connection may be made by a suitable adhesive, or a recess 74 can be formed in inner wall and the annulus inserted therein. The annulus also includes an inner wall 76 which defines a central opening 78 which is coaxial with aforementioned housing axis 20.

The disposable liner 16 is comprised of a generally rigid nontoxic material such as thermoplastic or paper which is formed into a hollow frusto-conical member 90 having an outer wall surface 92 and an inner wall surface 96. Member 90 has the same taper as opening 44 so that the liner 16 can lie against its inner wall 62 to be supported thereby.

The lower end of member 90 defines an opening 98. The upper end of member 90 defines a generally saddle shaped opening 104 which is curved to lie generally about an axis which is at a right angle to axis 20 (into the paper).

A second member 110 which may be comprised of a flexible, relatively thin material such as thermoplastic or paper is generally oval in shape and has an oval central opening 114.

Second member 110 is connected to first member 90 with the opening 114 in alignment with opening 104.

Alignment members 120 and 122 which are elongated ribs are radially outwardly directed and disposed in opposed diametrical relation to each other on outer wall 92 adjacent the second member 110. The alignment members 120 and 122 extend generally parallel to axis 20 and are disposed to lie along axis 106. The alignment members are similar in size to earlier mentioned recesses 58 and 60 in housing 14.

Suitable means may be used to connect the mouthpiece assembly 10 to the breathing apparatus. A particularly advantageous means may be a reduction fitting 130 which may preferably be made of nylon. The reduction fitting 130 comprises a cup shaped member 138 having an annular wall 140 whose inner diameter is the same as the outer diameter of portion 28. The bottom 142 of cup shaped member 138 includes an opening 146 which is coaxial with axis 20. A cylindrical skirt 150 having a central opening 152 extends downwardly from bottom 142. A tube 154 made of a suitable material such as stainless steel or the like is press fit into opening 152.

The reduction fitting 130 may be connected to the housing 14 by pressing cylindrical portion 28 into engagement with cup shaped member 138.

A hose or tube 160 may be slipped over the distal end of tube 154 to connect the mouth piece assembly 10 to a breathing apparatus.

The protective sheath 18 (FIG. 4) may be made of any suitable inexpensive material. In its present form the protective sheath 18 is a foldable paper bag 164 with an opening 166 formed in its closed end 168. The sides 170 of the bag 164 are at least as long as the housing 14.

Referring now to FIG. 1, it can be seen how the housing 14, liner 16 and protective sheath cooperate to form the mouth piece assembly 10.

The protective sheath 18 is placed over the housing 14 with the opening 166 in alignment with saddle shaped opening 104 and the sides 166 overlying the housing 14.

The liner is inserted through opening 166 and into the opening 44 in the housing 14. Since both the taper of the opening 44 in the housing and the taper of member 90 of the liner are the same, the liner 18 slips telescopically into the housing with the second member 110 being generally flat and lying against first curved surface 38 with its closed end 168 between them, the member 90 lies loosely against the inner wall 76 of annular seal 70. The alignment members 120 and 122 are partially received in recesses 58 and 60.

To use the mouthpiece assembly 10, the patient grasps the protective sheath 15 and housing 14. He presses the second member 110 against his pursed lips. This causes the liner 16 to move into the housing so that the second member 110 moves into contact with second curved surface 40 with the protective sheath 18 between them and the lower end of the liner to sealingly engaging the inner wall 78 of sealing member 70.

Alignment members 120 and 122 and recesses 58 and 60 form complimentary and mutually engagable guide means for retaining the housing 14 and liner 16 against rotation relative to each other around axis 20.

In this configuration air can be inhaled and exhaled with sustained force through the mouthpiece assembly 10 and into or out of the breathing apparatus (not shown) through hose 160 without air leaking from the system through the space between the outer wall 92 of the liner and the opening 44 in the housing 14 or from between the patient's lips and the mouthpiece.

The protective sheath 18 prevents the patient's hand from coming into contact with housing 14.

After use, the liner 16 and protective sheath 18 are discarded so that a new liner and protective sheath can be used for the next patient.

Figure 6:
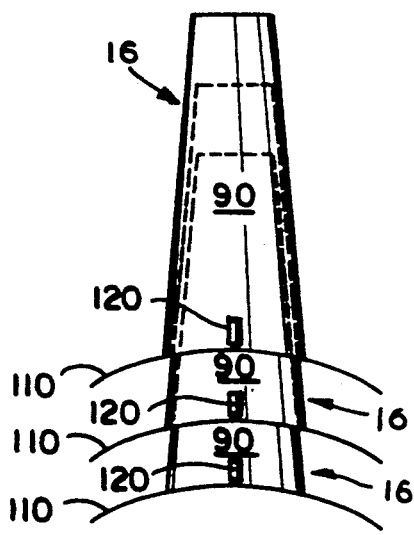
FIG. 6 is a view partially in section of a plurality of liners that are stacked for storage.

Because the liner is to be discarded after its use, it is important for the therapist to have a large number at hand. It is convenient for them to be stored in stacks to minimize the amount of space required as shown in FIG. 6. Thus each first member 90 is slidingly and telescopically received within the corresponding member 90 of the next adjacent liner 16. Alignment members 120 and 122 serve as spacers liners to prevent adjacent liners from jamming against each other while at the same time permitting easy withdrawal of a liner from the stack.

While the invention has been described with respect to a particular embodiment, it is apparent that other embodiments can be employed to achieve the inventive result. Thus, the scope of the invention should not be limited by the foregoing description, but, rather only by the scope of the claims appended hereto.

I claim:

1. A mouthpiece assembly for a breathing apparatus comprising a housing and a disposable liner, said housing including an inner wall defining an opening therethrough and said liner including a portion that is slidably received by and disposed in said opening in said housing, means on said housing defining a bearing surface, said liner including a member for engaging the lips of a patient using the breathing apparatus, said member being for lying against said bearing surface, seal means deposed between said housing and said liner, said seal means being operative to preventing air flow between said housing and said liner when said mouthpiece is used, and conduit means for connecting said housing to the breathing apparatus, 2. A mouthpiece as defined in claim 1 wherein said bearing surface comprises a first portion having a predetermined curvature and a second portion of flatter curvature, and said first portion of said bearing surface is formed within said second bearing surface so that a portion of said second bearing surface is disposed on on each side of said first bearing surface, said member for engaging the lips of a patient being supported by said first bearing surface and said seals means being operative to prevent air flow between said liner and said housing.

3. A mouthpiece assembly as defined in claim 2 wherein said seal means comprises an annular yieldable resilient member, the outer wall of said resilient member being connected to said inner wall of said housing and the inner wall of said resilient member being engagable with said portion of said liner.

4. A mouthpiece assembly as defined in claim 3 wherein said portion of said liner is hollow and frustoconical, said member for engaging the lips of a patient being connected at the larger end of said portion, said inner wall of said housing defining a conical opening, and the taper of said portion of said liner and said conical opening are the same so that said inner wall supports said liner when said mouthpiece is being used.

5. A mouthpiece assembly as defined in claim 4 including complementary mutually engagable guide means on said housing and on said liner, said guide means cooperating to prevent said liner and said housing from rotating relative to each other.

6. A mouthpiece assembly as defined in claim 1 including a protective sheath disposed in overlying relation to said housing.

7. A mouthpiece assembly as defined in claim 6 wherein said protective sheath comprises an end member and a side wall connected to said end wall and an opening in said end wall through which said portion is received.

8. A mouthpiece assembly as defined in claim 7 wherein said protective sheath is made from paper.

* * * * *